(12) United States Patent
Austic et al.

(10) Patent No.: US 9,422,584 B2
(45) Date of Patent: Aug. 23, 2016

(54) FATTY ACID ESTERIFICATION PROCESS

(75) Inventors: Greg Austic, Pittsboro, NC (US);
Rachel Burton, Pittsboro, NC (US);
Xiaohu Fan, Pittsboro, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/979,917

(22) PCT Filed: Feb. 6, 2012

(86) PCT No.: PCT/US2012/023927
§ 371 (c)(1),
(2), (4) Date: Dec. 19, 2013

(87) PCT Pub. No.: WO2012/106701
PCT Pub. Date: Aug. 9, 2012

(65) Prior Publication Data
US 2014/0120589 A1    May 1, 2014

Related U.S. Application Data

(60) Provisional application No. 61/439,412, filed on Feb. 4, 2011.

(51) Int. Cl.
*C12P 7/64* (2006.01)
*C12M 1/40* (2006.01)
*C12M 1/00* (2006.01)

(52) U.S. Cl.
CPC .............. *C12P 7/649* (2013.01); *C12M 21/18* (2013.01); *C12M 23/58* (2013.01); *Y02E 50/13* (2013.01)

(58) Field of Classification Search
None
See application file for complete search history.

(56) References Cited

U.S. PATENT DOCUMENTS

| | | |
|---|---|---|
| 2,588,435 A | 3/1952 | Van Loon et al. |
| 3,064,952 A | 11/1962 | Brown |
| 4,164,506 A | 8/1979 | Kawahara et al. |
| 6,822,105 B1 | 11/2004 | Luxem et al. |
| 7,087,771 B2 | 8/2006 | Luxem et al. |
| 2004/0186307 A1 | 9/2004 | Piacentini et al. |

FOREIGN PATENT DOCUMENTS

| | | |
|---|---|---|
| WO | 88/02775 A1 | 4/1988 |
| WO | 93/12241 A1 | 6/1993 |
| WO | 2008/125574 A1 | 10/2008 |

OTHER PUBLICATIONS

Jeong et al., Biotechnol Tech, vol. 11, No. 12, pp. 853-858 (1997).
Pastor et al., App Biochem and Biotech, vol. 50, 251-263.

*Primary Examiner* — Nashaat Nashed
(74) *Attorney, Agent, or Firm* — Kristin McNamara

(57) ABSTRACT

The invention relates to the utilization of fatty acid feedstocks with substantial free fatty acid content in the production of biodiesel by the use of microbial enzymes.

14 Claims, 1 Drawing Sheet

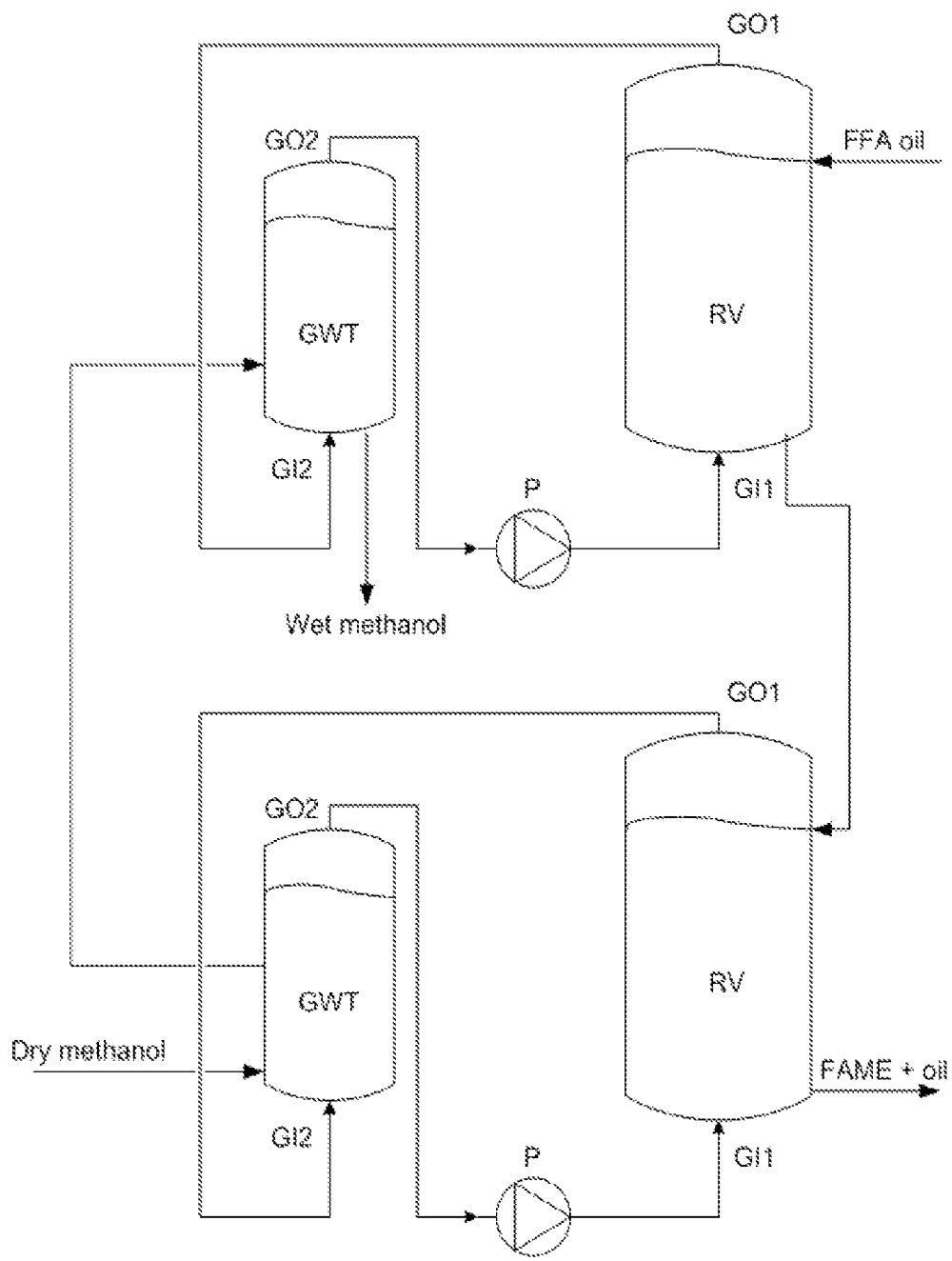

SEQUENCE LISTING

<160> NUMBER OF SEQ ID NOS: 1

<210> SEQ ID NO 1
<211> LENGTH: 342
<212> TYPE: PRT
<213> ORGANISM: Candida antarctica

<400> SEQUENCE: 1

```
Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
                20                  25                  30

Ala Phe Ser Gln Pro Lys Ser Val Leu Asp Ala Gly Leu Thr Cys Gln
            35                  40                  45

Gly Ala Ser Pro Ser Ser Val Ser Lys Pro Ile Leu Leu Val Pro Gly
        50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
                100                 105                 110

Thr Ala Leu Tyr Ala Gly Ser Gly Asn Asn Lys Leu Pro Val Leu Thr
            115                 120                 125

Trp Ser Gln Gly Gly Leu Val Ala Gln Trp Gly Leu Thr Phe Phe Pro
        130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
                180                 185                 190

Arg Asn Ala Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
        210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
                260                 265                 270

Ala Arg Ser Ala Asp Tyr Gly Ile Thr Asp Cys Asn Pro Leu Pro Ala
            275                 280                 285

Asn Asp Leu Thr Pro Glu Gln Lys Val Ala Ala Ala Leu Leu Ala
        290                 295                 300
```

-continued

```
Pro Ala Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
            325                 330                 335

Ser Gly Ile Val Thr Pro
            340
```

FATTY ACID ESTERIFICATION PROCESS

CROSS-REFERENCE TO RELATED APPLICATIONS

This application is a 35 U.S.C. 371 national application of PCT/US2012/023927 filed Feb. 6, 2012, which claims priority or the benefit under 35 U.S.C. 119 of U.S. provisional application No. 61/439,412 filed Feb. 4, 2011, the contents of which are fully incorporated herein by reference.

This invention was made with government support under Grant No. DE-SC0003402, awarded by the United States Department of Energy. The government has certain rights in the invention.

REFERENCE TO A SEQUENCE LISTING

This application contains a Sequence Listing in computer readable form, which is incorporated herein by reference.

FIELD OF THE INVENTION

The present invention relates to a process for preparing carboxylic acid derivatives. In particular the invention relates to the utilization of fatty acid feedstocks with substantial free fatty acid content in the production of biodiesel.

BACKGROUND OF THE INVENTION

As a result of the increasing interest in renewable resources in general and biofuels in particular, a number of processes has been developed for the production of esters of fatty acids and lower alcohols, which esters are also referred to as 'biodiesel'. Early 'biodiesel' processes prescribed the use of neutral raw materials and thereby competed with food applications. Accordingly, there is an incentive to exploit cheaper alternative sources of fatty acid moieties as raw material for biodiesel production. This often means that such fatty acid feedstocks may contain free fatty acids and that their FFA contents can vary over a wide range.

Before such fatty acid feedstock is suitable for use in a transesterification process for biodiesel production the FFA content needs to be reduced to ≤0.25%. This may be performed by esterifying the FFA with a lower alcohol. However, the esterification reaction is reversible and leads to an equilibrium where one of the products formed by the esterification is water. Shifting the reaction equilibrium to the ester side therefore requires either the use of a large excess of lower alcohol or the removal of the formed water.

Accordingly, U.S. Pat. No. 4,164,506 discloses a process comprising the esterification of free fatty acids of unrefined fats with a lower alcohol in an amount larger than its solubility in the fats in the presence of an acid catalyst. However, several lower alcohols have a boiling point that is lower than the boiling point of water which implies that it is impossible to remove the water formed by the esterification while retaining the lower alcohol in the reaction mixture. Shifting the esterification equilibrium to the ester side therefore requires the use of a large excess of lower alcohol.

This disadvantage can be overcome by using a high boiling alcohol such as glycerol as disclosed in U.S. Pat. No. 2,588,435. Using such high boiling alcohols has the additional advantage that the reaction can be carried out at a higher temperature, which increases the rate constant of the esterification reaction, without having to operate under superatmospheric pressure. In fact, as disclosed in U.S. Pat. No. 6,822,105, the esterification can now be carried out under vacuum, which promotes the evaporation of the water formed by the esterification reaction which is thereby shifted towards the ester side. The use of nitrogen during a vacuum stripping operation further facilitates the water evaporation.

However, as demonstrated by the examples in U.S. Pat. Nos. 6,822,105 and 7,087,771, the esterification reaction is quite slow and it can take some 7 to 11 hours before the acid value of the reaction mixture, which is indicative of the residual free fatty acid content, has decreased to a value below 0.4 (mg KOH per g oil), which in industrial practice is the maximum value for a starting material for a transesterification process leading to biodiesel. The example in U.S. Patent Application Publication No. 2004/0186307 employing a solid esterification catalyst, which is present in a packed bed inside the esterification reactor, also mentions a reaction time of 5 hours at a temperature of 200° C. Holding fatty materials at such a high temperature for long periods of time can lead to the formation of unwanted side-products.

Accordingly, there is a strong preference for an esterification reaction at lower temperatures and for a catalyst that does not cause side-products to be formed. Operating at a lower temperature can also lead to energy savings. In this context, the use of enzymes in general and of lipases in particular merits consideration. However, the use of enzymes is far from straightforward. Their activity depends on the water concentration but water also affects the position of the esterification equilibrium. Moreover, the reagents should be well mixed, which is why the literature often mentions the use of solvents, e.g., Pastor et al., 1994, *Applied Biochemistry and Biotechnology* 50: 251-263: Synthesis of Mono- and Dioleylglycerols Using an Immobilized Lipase. For industrial processes the use of solvents raises the cost of operation and is therefore preferably avoided.

WO 2008/125574 discloses an esterification process wherein the formed water is removed from the reaction mixture by stripping with an inert gas. However, there is further need for enzymatic processes that allows fatty raw materials with variable free fatty acid contents to be utilized as raw material for biodiesel production.

OBJECTS OF THE INVENTION

Accordingly, it is an object of the invention to overcome the various disadvantages of the prior art processes for utilizing fatty raw materials with a high free fatty acid content for the production of fatty acid esters of lower alcohols by the use of lipolytic enzymes.

It is another object of the invention to avoid the use of solvents.

It is also an object of the invention to use the lipolytic enzyme in such a way that its productivity is maximized.

It is a further object of the invention to enable the maximization of the yield of lower alkyl esters of fatty acids based on the fatty acid moiety content of the raw material.

It is a further object of the invention to enable the maximization of the yield of lower alkyl esters of fatty acids based on the lower alcohol consumption of the process.

It is a further object of the invention to enable the maximization of the yield of lower alkyl esters of fatty acids while minimizing the energy consumption of the process.

It is yet another object of the invention to provide a process that can accommodate a wide range of raw materials with varying free fatty acid contents.

These and further objects of the invention will become apparent from the description and the examples hereinafter.

SUMMARY OF THE INVENTION

It has surprisingly been found that in an esterification process where water is removed from the reaction mixture by stripping with an inert gas, the stripping gas, following drying by passage through a volume of a lower alcohol, can be reused.

It has furthermore surprisingly been found that in the above esterification process, the volume of a lower alcohol, following use for drying of the stripping gas, may be reused in a transesterification process, such as disclosed in WO 2006/072256, wherein some water is needed. The process of the invention may be applied in a biodiesel production process, a) to esterify the free fatty acids (FFA) in a glyceride feedstock to lower the FFA content sufficiently for allowing the feedstock with fatty acid esters to be used in a chemical catalyzed biodiesel process, b) to esterify the FFA in a glyceride feedstock originating from an enzymatic transesterification process to achieve the biodiesel standard of –0.25% FFA.

The advantage is a simplified total biodiesel production process wherein the "wet" lower alcohol from the esterification process of the invention does not have to be dewatered but can be reused at the biodiesel refinery in a transesterification process. This results in reduced energy consumption.

Accordingly, the invention provides a process for the production of fatty acid alkyl esters from a fatty acid feedstock comprising free fatty acids, comprising the steps of: a) providing a reaction mixture (R) that comprises the fatty acid feedstock, a lower alcohol, and a lipolytic enzyme; b) allowing the reaction mixture (R) to react under formation of fatty acids alkyl esters; wherein a gas flow (G) is passed through the reaction mixture (R), and thereafter passed through a volume of lower alcohol (A), before being recirculated through the reaction mixture (R). Furthermore, the invention provides a production system for processing a reaction mixture (R), said production system comprising:

(a) one or more enclosed reaction vessels(s) (RV) suitable for comprising said reaction mixture (R), each reaction vessels (RV) comprising at least one first gas inlet (GI1) and at least one first gas outlet (GO1), (b) one or more gas wash tank(s) (GWT) suitable for comprising a gas wash liquid (W), each gas wash tank (GWT) comprising at least one second gas inlet (GI2) and at least one second gas outlet (GO2), (c) comprising one or more gas pump(s) (P) capable of delivering a gas flow (G), which can be passed by the first gas inlet (GI1) through the reaction vessels (RV), discharged by the first gas outlet (GO1) and thereafter passed by the second gas inlet (GI2) through the gas wash liquid (GWL), and discharged by the second gas outlet (GO2), before being recirculated to the first gas inlet (GI1) into the reaction vessels (RV).

BRIEF DESCRIPTION OF THE DRAWINGS

FIG. 1 shows a production system suitable for performing the process of the present invention.

DETAILED DESCRIPTION OF THE INVENTION

Biodiesel

Fatty acid alkyl esters (FAAE) of short-chain alcohols, such as fatty acid methyl esters (FAME) and fatty acid ethyl esters (FAEE) are also called biodiesel, because they are used as an additive to or as a replacement of fossil diesel.

Alcohol

The alcohol used as gas wash liquid in the method of the invention is preferably a short-chain, branched or linear, alcohol having 1 to 5 carbon atoms ($C_1$, $C_2$, $C_3$, $C_4$, or $C_5$, "a lower alcohol") and mixtures thereof. Preferred lower alcohols are methanol, ethanol and propanol. The alcohol content is preferably less than 4, 3, 2, 1.5 or 1.0 molar equivalents to the amount of fatty acids in the reaction mixture (free and glyceride bound fatty acids). The alcohol may be added stepwise (such as in 1, 2, 3, 4, 5, 6, 7, 8, 9, 10 or more steps) and/or continuously to the reaction mixture.

Fatty Acid Feedstock

The term "fatty acid feedstock" is defined herein as a substrate comprising fatty acid derivatives. The substrate may comprise fatty acid alkyl esters, triglyceride, diglyceride, monoglyceride, free fatty acid or any combination thereof. Any oils and fats of vegetable or animal origin comprising fatty acids may be used as substrate for producing fatty acid alkyl esters in the process of the invention. Also fatty acid feedstock consisting substantially of fatty acid alkyl esters is suitable as feedstock (biodiesel feedstock) for the present invention. Preferably, the free fatty acid content of the fatty acid feedstock is above 0.25%, above 0.30%, above 0.35%, above 0.50%, above 0.75%, above 1.0%, above 5.0%, above 10.0%, above 15.0%, above 20.0%, above 25.0%, above 30.0%, above 40%, or even above 50.0%.

The fatty acid feedstock may be oil selected from the group consisting of: algae oil, canola oil, coconut oil, castor oil, coconut oil (copra oil), corn oil, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, and oil from halophytes, pennycress oil, camelina oil, jojoba oil, coriander seed oil, meadowfoam oil, seashore mallow oil, microbial oils or any combination thereof.

The fatty acid feedstock may be fat selected from the group consisting of: animal fat, including tallow from pigs, beef and sheep, lard, chicken fat, fish oil, or any combination thereof.

The fatty acid feedstock may be crude, refined, bleached, deodorized, degummed, or any combination thereof.

Food quality oils and fats are expensive, and therefore, waste and by-products from their processing as well as non-food grade oils and fats have become increasingly attractive feedstock for producing fatty acid alkyl ester. Soap stock is the fraction of oil obtained in an oil refinery by treating the oil with a base to convert free fatty acids to soaps (e.g., sodium soaps). The soap stock usually contains a fraction of glycerides beside the soaps. Acid oil is the by-product from the oil refinery produced by acidification of soap stock to solubilize the soaps. It mainly contains free fatty acids (FFA) and acylglycerols. Distillates like Palm Fatty Acid Distillate (PFAD) is the by-product from oil refining coming from a distillation process used to eliminate free fatty acid from the oil.

The feedstock may be an intermediate product, a waste product or a by-product of oil or fat refining selected from the group consisting of: soap stock; acid oil; fatty acid distillates such as PFAD, soy fatty acid distillate, rapeseed fatty acid distillate, rice bran fatty acid distillate, poultry fat fatty acid distillate, beef tallow fatty acid distillate, etc.; gums from degumming; by-products from the production of omega-3 fatty acids derivates from fish oil; fat trap grease; yellow grease, and brown grease, free fatty acids like oleic acid; or fractions of oil obtained by physical separations; or any combinations thereof.

The process of the invention provides an economic and environmentally friendly alternative to the use of the acid catalyzed esterification processes that are currently used as it can accommodate raw materials with widely different FFA contents. These can be crude or degummed oils and fats of vegetable or animal origin and preferably those that have such a high FFA content that their neutralization by conventional means is uneconomic. High acidity rice bran oil is a prime example of such oils, but palm oil may occasionally also exhibit high FFA contents. In general, oils and fats that are used for the production of soap because their FFA content is too high for economic use as food are suitable.

The FFA contents of the raw materials mentioned above can vary widely. Crude rice bran oil for example can have an FFA content of more than 10%, even more than 20% or even more than 30%. Fatty acid distillates originating from the physical refining process can contain in excess of 90% FFA; it is an advantage of the process of the invention that it can effectively handle all these raw materials.

Reactor Design

The process of the invention is preferably performed in a reactor (i.e., a production system) in which the catalyst is freely distributed in the reaction mixture. The process may apply a heterogeneous catalyst or a homogeneous catalyst, e.g., an immobilized enzyme composition, or a liquid enzyme composition.

A gas flow serves to remove volatile reaction products, for example water in esterification reactions from the reaction mixture, and hence to shift the equilibrium to the product side. The gas flow further serves to mix the reaction mixture. In a preferred embodiment wherein a homogeneous catalyst, e.g., an immobilized enzyme composition, is applied, the gas flow serves to keep the heterogeneous catalyst suspended and in contact with the reaction mixture. In another preferred embodiment using a homogeneous liquid catalyst, such as a liquid enzyme, effective mixing increases contact between the polar and non-polar phases, decreasing total reaction time.

A rotary jet head (EP 1324818) may be used to mix the gas flow into the reaction mixture as well as providing efficient mixing of the reaction mixture.

As the gas flow (G) thereafter is passed through a volume of a lower alcohol (A), e.g., comprised in a column, the gas releases the volatile reaction product (e.g., water) to the lower alcohol (A), and the so dried gas can be recirculated through the reaction mixture (R).

The reactor may further be equipped with a stirrer in order to increase the mixing of the reaction mixture.

During step (b) the temperature of the reaction mixture (R) is preferably kept between 25° C. and 80° C., more preferably between 30° C. and 50° C., and most preferably between 35° C. and 45° C.

The volume of lower alcohol (A) may comprises the same lower alcohol as comprised in the reaction mixture (R). However, for biodiesel production more than one lower alcohol as well as a mixture of two or more lower alcohols may be applied.

The volume of lower alcohol (A) will over time accumulate the volatile reaction product (e.g., water), and the process efficiency will decrease. Preferably the amount of water in the volume of lower alcohol (A) is 70% or less, 65% or less, 60% or less, 55% or less, 50% or less, 45% or less, 40% or less, 35% or less, 30% or less, more preferably 25% or less, even more preferably 20%, 15%, 10% or less.

The temperature control on the volume of the lower alcohol determines the moisture equilibrium in the production system. Lower temperatures will result in a lower moisture equilibrium and higher temperatures will result in a higher moisture equilibrium in the production system. In a preferred embodiment wherein the lower alcohol is methanol the temperature of the volume of the lower alcohol (A) is between 25° C. and 35° C., preferably around 30° C.

The lower alcohol may undergo distillation, pervaporation or other suitable separation technique where after it can be reused in the process of the invention. The water-containing lower alcohol without any separation may also be reused as a reactant in the transesterification of triglycerides, where some water is needed and excess water will be leaving the product stream in the glycerol phase.

A production system suitable for performing the process of the present invention may comprise (a) one or more enclosed reaction vessels(s) (RV) suitable for comprising said reaction mixture (R), each reaction vessels (RV) comprising at least one first gas inlet (GI1) and at least one first gas outlet (GO1), (b) one or more gas wash tank(s) (GWT) suitable for comprising a gas wash liquid (W), each gas wash tank (GWT) comprising at least one second gas inlet (GI2) and at least one second gas outlet (GO2), (c) comprising one or more gas pump(s) (P) capable of delivering a gas flow (G), which can be passed by the first gas inlet (GI1) through the reaction vessels (RV), discharged by the first gas outlet (GO1) and thereafter passed by the second gas inlet (GI2) through the gas wash liquid (GWL), and discharged by the second gas outlet (GO2), before being recirculated to the first gas inlet (GI1) into the reaction vessels (RV). The gas pump applied in the above production system may be any device suitable for creating a gas flow, e.g., by physical or mechanical action.

In an embodiment of the process of the invention wherein a homogeneous catalyst is applied in a continuous reactor, the polar phase (in which the catalyst is dissolved) may be isolated using gravity separation or mechanical separation after exiting the reactor vessel. After separation, the polar phase may be recycled back to the reactor. To replace any catalyst loss through deactivation or imperfect separation an amount of catalyst may be added continuously or stepwise to the recycled stream.

In a preferred embodiment of the process of the present invention, the process is performed in the above production system and the reaction mixture comprises fatty acid feedstock, a lower alcohol, and a lipolytic enzyme, and the gas wash liquid is a lower alcohol, e.g., methanol or ethanol.

The Gas

According to the invention, the gas or gasses used may be any inert gas, i.e., a gas that does not react with the reactants, the catalyst or the reactor materials. Preferably the gas is atmospheric air, oxygen, nitrogen, noble gases or carbon dioxide, or any mixture thereof. The gas used can be supplied from suitable pressure vessels or pumps, for example gas bottles, or by means of compressors.

Catalyst

The use of heterogeneous catalysts has the advantage that they can be removed in a simple manner after the reaction and if appropriate reused. Examples of such heterogeneous catalysts are metal salts, ion exchange resins or catalysts immobilized on suitable supports. Particularly suitable catalysts are those with particle sizes which allow simple and rapid removal from the reaction medium, e.g., enzymes, which are immobilized on supports. The supports used for enzyme immobilization are frequently ion exchange resins or polymer particles which possess suitable particle size distributions.

The catalysts used in accordance with the invention may be those whose particle size is such that they can be retained in the reaction vessel without any great pressure drop using the customary available filter systems, i.e., larger than 0.5 μm, preferably larger than 5 μm, more preferably larger than 10 μm, especially larger than 25 μm. They may be polymeric catalysts of appropriate particle size, or catalysts immobilized on suitable supports. Examples of the polymeric catalysts are ion exchangers, for example sulphonated polystyrenes or zeolites. According to the invention, the catalysts immobilized on suitable supports may be chemical catalysts or immobilized enzymes.

In embodiments where a homogeneous catalyst is applied the catalyst is preferably in solution with a high boiling point liquid, preferably glycerol. The reaction takes place at the interface layer between the polar and non-polar phases. The byproduct water is stripped from the solution by the gas flow (G), though at a slightly reduced rate as compared to a heterogeneous system due to the presence of a high boiling point polar phase (e.g., glycerol). The polar phase may be recovered from the non-polar phase downstream of the reactor by simple gravity or mechanical separation methods and returned to the reactor vessel.

The homogeneous catalysts used in the process of the invention are preferably an enzymatic catalyst, e.g., a lipase from *Thermomyces lanuginosus* (TL) or *Candida antarctica* Lipase B (CALB) in glycerol solutions, using glycerol as the high boiling point polar phase.

Enzyme Immobilization

The use of immobilized enzymes in processing of oils experience significant growth due to new technology developments that have enabled cost effective methods. A fundamental advantage of immobilized enzymes is that they can be recovered and re-used from a batch process by simple filtration.

Various ways of immobilizing lipolytic enzymes are well known in the art. A review of lipase immobilization is found in "Immobilized lipase reactors for modification of fats and oils—a review" Malcata et al., 1990, *J. Am. Oil Chem. Soc.* 67: 890-910, where examples of representative lipase immobilizing carriers are illustrated, including inorganic carriers such as diatomaceous earth, silica, porous glass, etc.; various synthetic resins and synthetic resin ion exchangers; and natural polysaccharide carriers such as cellulose and cross-linked dextrin introduced with ion exchange groups.

In some embodiments, the invention relates to a method, wherein the lipolytic enzyme is immobilized either on a carrier; by entrapment in natural or synthetic matrices, such as sol-gels, alginate, and carrageenan; by cross-linking methods such as in cross-linked enzyme crystals (CLEC) and cross-linked enzyme aggregates (CLEA); or by precipitation on salt crystals such as protein-coated micro-crystals (PCMC).

In some embodiments, the invention relates to a method, wherein the carrier is a hydrophilic carrier selected from the group containing: porous inorganic particles composed of alumina, silica or silicates such as porous glas, zeolites, diatomaceous earth, bentonite, vermiculite, hydrotalcite; and porous organic particles composed of carbohydrate polymers such as agarose or cellulose.

In some embodiments, the invention relates to a method, wherein the carrier is a hydrophobic carrier selected from the group containing: synthetic polymers such as nylon, polyethylene, polypropylene, polymethacrylate, or polystyrene; and activated carbon.

Enzyme

The lipolytic enzyme may be selected from lipases, cutinases or esterases, for example a lipase selected from the *Candida antarctica* lipase A (CALA) as disclosed in WO 88/02775, the *C. antarctica* lipase B (CALB) as disclosed in WO 88/02775 and shown in SEQ ID NO:1 herein, the *Thermomyces lanuginosus* (previously *Humicola lanuginosus*) lipase disclosed in EP 258068), the *Thermomyces lanuginosus* variants disclosed in WO 2000/60063 or WO 95/22615, in particular the lipase shown in positions 1-269 of SEQ ID NO: 2 of WO 95/22615, the *Hyphozyma* sp. lipase (WO 98/18912), and the *Rhizomucor miehei* lipase (SEQ ID NO: 5 in WO 2004/099400), a lipase from *P. alcaligenes* or *P. pseudoalcaligenes* (EP 218272), *P. cepacia* (EP 331376), *P. glumae*, *P. stutzeri* (GB 1,372,034), *P. fluorescens*, *Pseudomonas* sp. strain SD 705 (WO 95/06720 and WO 96/27002), *P. wisconsinensis* (WO 96/12012); a *Bacillus* lipase, e.g., from *B. subtilis* (Dartois et al., 1993, *Biochemica et Biophysica Acta* 1131: 253-360), *B. stearothermophilus* (JP 64/744992) or *B. pumilus* (WO 91/16422). Also preferred is a lipase from any of the following organisms: *Absidia corymbefera*, *Absidia reflexa*, *Aspergillus niger*, *Aspergillus oryzae*, *Aspergillus tubingensis*, *Fusarium heterosporum*, *Fusarium oxysporum*, *Penicillium camembertii*, *Rhizopus delemar* (*oryzae*), *Aspergillus foetidus*, *Rhizomucor miehei*, and *Thermomyces lanuginosus*, such as a lipase selected from any of SEQ ID NOs: 1 to 15 in WO 2004/099400.

Preferably, the lipolytic enzyme is an enzyme having at least 60%, at least 70%, at least 80%, at least 90%, at least 95%, at least 96%, at least 97%, at least 98%, or even at least 99% identity to any of the aforementioned lipases.

More preferred, the lipolytic enzyme has at least 60%, at least 70%, at least 80%, at least 90%, at least 95%, at least 96%, at least 97%, at least 98%, at least or even at least 99% identity to the amino acid sequence shown as positions 1-342 of SEQ ID NO: 1 herein.

Liquid (non-immobilized or free) lipolytic enzyme compositions suitable for use in the process of the invention and examples of commercially available immobilized lipolytic enzyme include the ones sold under the trade names LIPOZYME TL 100 L, LIPOZYME CaLB L, CALLERA ULTRA L, and CALLERA TRANS from Novozymes A/S, Bagsvaerd, Denmark.

Immobilized lipolytic enzyme compositions suitable for use in the process of the invention and examples of commercially available immobilized lipolytic enzyme include the ones sold under the trade names NOVOZYM 435, LIPOZYME RM IM or LIPOZYME TL IM from Novozymes A/S, Bagsvaerd, Denmark, or Amano PS, from Amano, Japan.

Typically, the enzyme is used in a concentration corresponding to 1 LU/g fatty acid feedstock to 1000 LU/g fatty acid feedstock. Preferably the enzyme is used in a concentration of between 5 LU/g fatty acid feedstock to 500 LU/g fatty acid feedstock, more preferably between 10 LU/g fatty acid feedstock to 100 LU/g fatty acid feedstock.

Typically, the enzyme is used in a concentration corresponding to 1 PLU/g fatty acid feedstock to 1000 PLU/g fatty acid feedstock. Preferably the enzyme is used in a concentration of between 5 PLU/g fatty acid feedstock to 500 PLU/g fatty acid feedstock, more preferably between 10 PLU/g fatty acid feedstock to 100 PLU/g fatty acid feedstock.

Enzyme sources and formulation: The lipolytic enzyme used in the process of the invention may be derived or obtainable from any of the sources mentioned herein. The term "derived" means in this context that the enzyme may have been isolated from an organism where it is present natively, i.e., the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g., having one or more amino acids which are deleted, inserted and/or substituted, i.e., a recombinantly produced enzyme which is a mutant and/or a fragment of a native amino acid sequence. Within the meaning of a native enzyme are included natural variants. Furthermore, the term "derived" includes enzymes produced synthetically by, e.g., peptide synthesis. The term "derived"

also encompasses enzymes which have been modified, e.g., by glycosylation, phosphorylation etc., whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by, e.g., peptide synthesis. With respect to recombinantly produced enzyme the terms "obtainable" and "derived" refers to the identity of the enzyme and not the identity of the host organism in which it is produced recombinantly.

Accordingly, the lipolytic enzyme may be obtained from a microorganism by use of any suitable technique. For instance, an enzyme preparation may be obtained by fermentation of a suitable microorganism and subsequent isolation of an enzyme preparation from the resulting fermented broth or microorganism by methods known in the art. The enzyme may also be obtained by use of recombinant DNA techniques. Such method normally comprises cultivation of a host cell transformed with a recombinant DNA vector comprising a DNA sequence encoding the enzyme in question and the DNA sequence being operationally linked with an appropriate expression signal such that it is capable of expressing the enzyme in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

The optimum parameters for enzymatic activity will vary depending upon the enzyme used. The rate of enzyme degradation depends upon factors known in the art, including the enzyme concentration, substrate concentration, temperature, the presence or absence of inhibitors and presence of water. These parameters may be adjusted to optimise the esterification reaction.

During the enzymatic treatment step, the temperature of the suspension should be adjusted to provide effective enzyme activity. In general, a temperature of about 30° C. to about 90° C. is used, particularly from about 35° C. to about 60° C.

MATERIALS AND METHODS

Degree of Identity

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

Lipolytic Activity

Lipase Unit (LU): The lipolytic activity may be determined using tributyrine as substrate. This method is based on the hydrolysis of tributyrin by the enzyme, and the alkali consumption to keep pH constant during hydrolysis is registered as a function of time.

One Lipase Unit (LU) is defined as the amount of enzyme which, under standard conditions (i.e., at 30° C.; pH 7.0; with 0.1% w/v Gum Arabic as emulsifier and 0.16 M tributyrine as substrate) liberates 1 micromol titrable butyric acid per minute. One KLU is 1000 LU.

Propyl Laurate Units: The ester synthesis activity of immobilized lipases may be determined as Propyl Laurate Units per gram product: PLU/g.

The immobilized lipase esterifies lauric acid with 1-propanol, forming propyl laurate. The activity ($\mu$mol/g/min) is determined by quantification of formed propyl laurate and consumed lauric acid by GC. Reaction temperature is 60° C. and reaction time 20 min.

One PLU unit corresponds to 1 $\mu$mol/g/min, e.g., 1 $\mu$mol propyl laurate formed per g of enzyme product per minute.

Enzyme

NOVOZYM 435 is a commercial enzyme product from Novozymes A/S comprising an immobilized lipase B from *Candida antarctica* (SEQ ID NO:1 herein). The product has an activity of 10000 PLU/g. NOVOZYM 435 was used in Examples 1-5.

CALLERA ULTRA L is a commercial enzyme product from Novozymes A/S comprising an liquid lipase B from *Candida antarctica* (SEQ ID NO: 1 herein). The product has an activity of 50 KLU/g. CALLERA ULTRA L was used in Example 6.

Example 1

Esterification of free fatty acids from high FFA feedstock was performed using three different methods of eliminating water from the reaction mixture:

1. A process of the invention with continuous water removal
2. Vacuum/evaporation and refill with alcohol after the vacuum step
3. Heat/evaporation and refill with alcohol after the heat step The feedstock was yellow grease with 14.1% of FFA. Batch size was 40 g oil. Methanol was used as the alcohol. The amount of water in the reaction mixture at time=0 was 891 ppm. The enzyme was Novozym 435 in a dosage of 4% w/w of oil. The reaction was performed at a temperature of 45° C. with shaking at 300 rpm.

In the process of the invention, an air flow rate of 617 ml/min was applied and re-circulated in a 20 ml methanol column.

The vacuum/evaporation treatment was carried out in a rotary evaporator at 65° C. at 50 mbar for 3 hours after 30 and 60 minutes reaction time, respectively.

The heat/evaporation treatment used warm storage at 50° C. overnight in an open vessel to evaporate water and alcohol. In the two latter methods methanol was added to make up for the amount lost during evaporation. The results are presented in table 1.

TABLE 1

| Method | Reaction time, minutes | Vol % MeOH added | Water ppm (w/w) | % FFA |
|---|---|---|---|---|
| 1 | 30 | 1.69 | n.a. | 2.85 |
| 2 | 30 | 2.87 | 4632 | 3.08 |
| 3 | 30 | 2.87 | 4988 | 3.27 |
| 1 | 60 | 1.69 | n.a. | 0.88 |
| 2 | 60 | 4.66 | 1328 | 0.63 |
| 3 | 60 | 6.74 | 2325 | 0.89 |
| 1 | 100 | 1.69 | 577 | 0.25 |
| 2 | 105 | 6.50 | 309 | 0.38 |

Only with the process of the invention was it possible to achieve ≤0.25% FFA as required for biodiesel. Also, the amount of alcohol used in methods 2 and 3 are higher than method 1 which will cost more in a production setting. Lastly, the process of the invention is the only method of the three that are operating continuously and therefore having a shorter total operating time. In method 2 two interruptions for vacuum treatment were used and in method 3 one (long) heating/settling period was used.

Example 2

Esterification of free fatty acids in a biodiesel feedstock with 4.0% unconverted FFA feedstock was performed using two different methods for eliminating water from the reaction mixture:
1. A process of the invention with continuous water removal
2. Vacuum treatment and refill with alcohol The setup was as described in example 1. Four vacuum steps were used after 15, 30, 45, and 60 minutes, respectively. The water content in the reaction mixture at time=0 was 500 ppm. The results are presented in table 2.

TABLE 2

| Method | Reaction time, minutes | Vol % MeOH added | Water ppm | % FFA |
|---|---|---|---|---|
| 1 | 30 | 0.49 | n.a. | 0.83 |
| 2 | 30 | 0.80 | 1225 | 1.43 |
| 1 | 50 | 0.49 | n.a. | 0.30 |
| 2 | 60 | 7.88 | 260 | 0.54 |
| 1 | 65 | 0.49 | 129 | 0.17 |
| 2 | 90 | 7.88 | 348 | 0.49 |

Only with the process of the invention was it possible to achieve ≤0.25% FFA. The result was achieved with a low consumption of methanol.

Example 3

In this example we tested the efficiency of the invention to supply alcohol from the alcohol column to the reactor by the re-circulation of air. The feedstock was yellow grease with 15.44% FFA. All other conditions were as in example 1, treatment 1. The results are presented in table 3.

TABLE 3

| Reaction time, minutes | Vol % MeOH added | Water ppm (w/w) | % FFA |
|---|---|---|---|
| 15 | 0 | n.a. | 6.18 |
| 30 | 0 | 680 | 1.34 |
| 40 | 0 | n.a. | 0.52 |
| 60 | 0 | n.a. | 0.20 |
| 80 | 0 | n.a. | 0.18 |

The amount of methanol transferred from the methanol column by the air re-circulation was sufficient to obtain ≤0.25% FFA.

Example 4

The conditions are as in example 3 except that methanol was substituted with ethanol. The results are presented in table 4.

TABLE 4

| Reaction time, minutes | Vol % EtOH added | Water ppm (w/w) | % FFA |
|---|---|---|---|
| 15 | 0 | n.a. | 8.85 |
| 30 | 0 | 610 | 3.00 |
| 40 | 0 | n.a. | 1.57 |
| 60 | 0 | n.a. | 0.38 |
| 80 | 0 | n.a. | 0.21 |

Example 5

The conditions are as in examples 3 and 4 except that the feedstock is a biodiesel feedstock consisting of yellow grease FAME with 15% FFA added. The results are presented in table 5.

TABLE 5

| | Methanol | | Ethanol | |
|---|---|---|---|---|
| Reaction time, minutes | Water ppm (w/w) | % FFA | Water ppm (w/w) | % FFA |
| 15 | n.a. | 4.41 | n.a. | 8.39 |
| 30 | 530 | 0.82 | 569 | 3.05 |
| 40 | n.a. | 0.44 | n.a. | 1.32 |
| 60 | n.a. | 0.11 | n.a. | 0.30 |
| 80 | n.a. | 0.04 | n.a. | 0.20 |
| 100 | n.a. | 0.12 | n.a. | 0.18 |
| 120 | 52 | 0.09 | 76 | 0.17 |

Example 6

In this example a liquid enzyme composition, commercially sold as Lipozyme CALB-L. 40 grams of neat biodiesel doped with oleic acid to 2.1% FFA, 1 wt % (0.4 g) Lipozyme CALB-L, 2.57% (1.026 g) methanol, and 9-10% ACS grade glycerol were combined in a 120 ml bottle. The mixtures were reacted in a heated shaker at 300 rpm and 35° C. for 220 minutes. Samples were tested for % FFA at 50, 105, 165, and 220 minutes. Before sampling, the mixture was allowed to settle for 2 minutes to ensure no enzyme or glycerol was removed in the sample. The results are presented in Table 6. Three methods were tested:
 Method 1: A process of the invention for continuous water removal as described in example 1 with 10% (4 g) glycerol;
 Method 2: Addition of 10% glycerol (no continuous water removal);
 Method 3: Addition of 9% (3.6 g) glycerol and 1% (0.4 g) water (no continuous water removal).

TABLE 6

| Time (min.) | Method 1 (% FFA) | Method 2 (% FFA) | Method 3 (% FFA) |
|---|---|---|---|
| 0 | 2.10 | 2.10 | 2.10 |
| 50 | 1.40 | 1.90 | 1.96 |
| 105 | 0.71 | 1.60 | 1.81 |

TABLE 6-continued

| Time (min.) | Method 1 (% FFA) | Method 2 (% FFA) | Method 3 (% FFA) |
|---|---|---|---|
| 165 | 0.38 | 1.37 | 1.68 |
| 220 | 0.23 | 1.58 | 1.17 |

The invention claimed is:

1. A process for the production of fatty acid alkyl esters from a fatty acid feedstock containing free fatty acids, comprising the steps of:
   (a) providing a reaction mixture (R) that comprises the fatty acid feedstock, an alcohol having 1 to 5 carbon atoms, and a lipolytic enzyme;
   (b) allowing the reaction mixture (R) to react under formation of fatty acids alkyl esters;
   wherein a gas flow (G) is passed through the reaction mixture (R) and thereafter passed through a volume of alcohol having 1 to 5 carbon atoms (A), before being recirculated through the reaction mixture (R), and
   in which the alcohol having 1 to 5 carbon atoms comprised in the reaction mixture (R) is supplied without dewatering from the volume of alcohol having 1 to 5 carbon atoms (A) by the gas flow (G).

2. The process according to claim 1, wherein the alcohol having 1 to 5 carbon atoms is selected from methanol, ethanol, and propanol, and mixtures thereof.

3. The process according to claim 1 in which the gas comprises atmospheric air.

4. The process according to claim 1 in which the lipolytic enzyme is a lipase or a cutinase.

5. The process according to claim 1 in which the lipase is the *Candida antarctica* lipase B, such as an enzyme having at least 80% identity to the amino acid sequence shown as SEQ ID NO: 1.

6. The process according to claim 1 in which the lipolytic enzyme is applied in a liquid composition.

7. The process according to claim 1 in which the lipolytic enzyme is immobilized on a support.

8. The process according to claim 1 in which the process is performed as a batch, or a continuous process.

9. The process according to claim 1 in which the volume of alcohol having 1 to 5 carbon atoms (A) comprises the same lower alcohol as comprised in the reaction mixture (R).

10. The process according to claim 1, further comprising the step of reusing the volume of alcohol having 1 to 5 carbon atoms (A).

11. The process according to claim 1 in which the temperature of the reaction mixture (R) in step (b) is kept between 25° C. and 80° C.

12. The process according to claim 1 in which the reaction mixture (R) is stirred.

13. The process according to claim 1 comprising dispersing the gas flow (G) the reaction mixture (R) with a rotary jet head.

14. The process according to claim 1, in which the gas is selected from oxygen, nitrogen, noble gases, carbon dioxide, or any mixture thereof.

* * * * *